United States Patent [19]

Croci et al.

[11] Patent Number: 5,266,573

[45] Date of Patent: Nov. 30, 1993

[54] TRIFLUOROMETHYLPHENYLTETRAHYDROPYRIDINES FOR THE TREATMENT AND/OR PROPHYLAXIS OF INTESTINAL MOTILITY DISORDERS

[75] Inventors: Tiziano Croci; Alberto Bianchetti, both of Milan; Luciano Manara, Pietra Marazzi, all of Italy

[73] Assignee: Elf Sanofi, Paris, France

[21] Appl. No.: 38,082

[22] Filed: Mar. 29, 1993

Related U.S. Application Data

[60] Continuation of Ser. No. 836,251, Feb. 18, 1992, abandoned, which is a division of Ser. No. 563,196, Aug. 6, 1990, Pat. No. 5,109,005.

[30] Foreign Application Priority Data

Aug. 7, 1989 [FR] France ............... 89 10617

[51] Int. Cl.$^5$ ............. C07D 211/70; A61K 31/44
[52] U.S. Cl. .................... 514/277; 546/346
[58] Field of Search ............ 546/346; 514/277

[56] References Cited

U.S. PATENT DOCUMENTS 4,213,989 7/1980 Nedelec et al. ............ 546/346
4,521,428 6/1985 Nisato et al. ............. 546/346

Primary Examiner—C. Warren Ivy
Assistant Examiner—Phyllis G. Spivack
Attorney, Agent, or Firm—Bacon & Thomas

[57] ABSTRACT

A method of prophylaxis and/or treatment of intestinal motility disorders, in particular of constipation, in mammals which comprises administering to a mammal in need of such a treatment a prophylactically and/or therapeutically effective amount of a compound of formula (I)

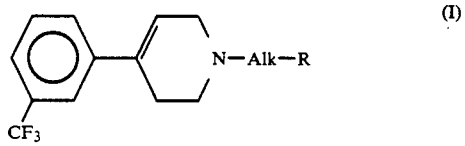

wherein

Alk represents a straight or branched ($C_1$-$C_4$)alkylene radical, and

R represents a cyano, acetyl, ($C_3$-$C_7$)cycloalkyl, phenyl, p-tolyl, pyridyl, pyridyl 1-oxide, or naphthyl group, or of a pharmaceutically acceptable salt thereof.

5 Claims, No Drawings

TRIFLUOROMETHYLPHENYLTETRAHYDROPYRIDINES FOR THE TREATMENT AND/OR PROPHYLAXIS OF INTESTINAL MOTILITY DISORDERS

This application is a Continuation of application Ser. No. 07/836,251, filed Feb. 18, 1992, now abandoned, which is a Division of application Ser. No. 07/563,196, filed Aug. 6, 1990, which is now U.S. Pat. No. 5,109,005.

The present invention relates to the use of certain trifluoromethylphenyltetrahydropyridines and their pharmaceutically acceptable salts in a method of treatment and/or prophylaxis of intestinal motility disorders and in particular of constipation.

European patents EP-B-60,176 and EP-B-101,381 disclose N-substituted trifluoromethylphenyltetrahydropyridines with anorectic activity.

It has now been found that said trifluoromethylphenyltetrahydropyridines have an intestinal prokinetic activity and they can therefore be useful in the treatment and/or prophylaxis of intestinal motility disorders and particularly in the treatment and/or prophylaxis of constipation.

It has also been found that their action on intestinal disorders and their anticonstipant activity are produced at doses remarkably lower than those which give anorexia.

It has finally been found that, at doses effective against constipation, the anticonstipant activity of said compounds, is not accompanied by sedative effects.

Therefore, in a first aspect, the present invention refers to a method of prophylaxis and/or treatment of intestinal motility disorders in mammals which comprises administering to a mammal in need of such prophylaxis and/or treatment, a prophylactically and/or therapeutically effective amount of a trifluoromethylphenyltetrahydropyridine of formula (I)

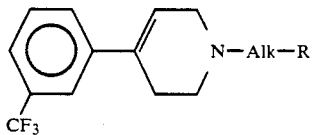

(I)

wherein

Alk represents a straight or branched $(C_1-C_4)$alkylene radical, and

R represents a cyano, acetyl, $(C_3-C_7)$cycloalkyl, phenyl, p-tolyl, pyridyl, pyridyl 1-oxide, or naphthyl group, or of a pharmaceutically acceptable salt thereof.

In a second aspect, the present invention relates to a pharmaceutical composition for the prophylaxis and/or the treatment of intestinal motility disorders in mammals which comprises a prophylactically and/or therapeutically effective amount of a trifluoromethylphenyltetrahydropyridine of formula (I) wherein Alk and R are as defined above, or of a pharmaceutically acceptable salt thereof.

As defined herein, the term "pyridyl" includes 2-pyridyl, 3-pyridyl, and 4-pyridyl radicals, and the term "naphthyl" includes both 1-naphthyl and 2-naphthyl radicals.

A preferred group of compounds for the use in the method according to the present invention comprises those compounds of formula (I) wherein Alk represents an ethylene radical which may optionally be substituted with one or two methyl groups and R is as defined above, and the pharmaceutically acceptable salts thereof.

The compounds of formula (I) and their preparation are described in EP-B-60,176, EP-B-101,381, and FR-86403 (a certificate of addition to FR-B-1,421,208).

The compound of formula (I) wherein ALk is an ethylene radical and R is a p-tolyl group, as well as the corresponding pharmaceutically acceptable salts, are novel and represent with the pharmaceutical compositions containing them further specific objects of the present invention.

The active principles to be used in the method according to the present invention, have been submitted to a test aimed at evaluating fecal excretion in rats, and showed a good intestinal prokinetic activity.

According to said test, male rats (Crl:CD - 220–250 g body weight) were placed at 8 a.m. in individual grid-floor contention cages. They were fasted during the test session while water was provided ad libitum. At 11:30 a.m. the test compounds were administered to the animals either orally or subcutaneously. The treatment schedule had been planned by means of random tables and groups of 8 animals each. At the time of drug treatment, rat rectal lumen was manually emptied from residual feces by gentle pressure and the rats were then placed again in the same cages. Fecal pellets were then collected 90 minutes after s.c. drug treatment or 210 minutes after p.o. drug treatment, their number was determined and their wet weight measured. The fecal pellets were then dried in an oven at 40° C. for 10 hours and weighed again to determine their dry weight. After 5–6 hours, the weight did not change any longer, the feces containing approximately the same percent residual humidity.

The parameter used to evaluate the activity of the test compounds was the dry weight of the feces excreted during 90 minutes (s.c.) or 210 minutes (p.o.) starting from administration of the test compound.

Statistical analysis of the obtained results used the Duncan new multiple analysis test.

The potency of the test compounds is expressed, by means of an activity index (AI-1 g), as the dose of test compound which induces the excretion of 1 g (dry weight) of feces. Said index is extrapolated from the log dose/activity regression line (p<0.05). Almost no fecal excretion has been observed in the concomitantly tested control animals which received the vehicle only. In the animals treated with high doses of test compounds, a maximum excretion of 12 to 16 fecal pellets with a dry weight of from about 1.4 to about 1.8 g, could be attained. With total excretions exceeding the above values, diarrhoea is observed and a correct quantification is impossible.

In the Table below, the AI-1 g of the following, representative compounds of formula (I) is reported:

1-(2-cyanoethyl)-4-(3-trifluoromethylphenyl)-1,2,3,6-tetrahydropyridine hydrochloride (Compound A)

1-[2-(2-naphthyl)ethyl]-4-(3-trifluoromethylphenyl)-1,2,3,6-tetrahydropyridine hydrochloride (Compound B)

1-[2-(1-naphthyl)ethyl]-4-(3-trifluoromethylphenyl)-1,2,3,6-tetrahydropyridine hydrochloride (Compound C)

1-(2-phenylethyl)-4-(3-trifluoromethylphenyl)-1,2,3,6-tetrahydropyridine hydrochloride (Compound D)

1-[2-(2-pyridyl)ethyl]-4-(3-trifluoromethylphenyl)-1,2,3,6-tetrahydropyridine dihydrochloride (Compound E)

1-[2-(3-pyridyl)ethyl]-4-(3-trifluoromethylphenyl)-1,2,3,6-tetrahydropyridine monohydrate dihydrochloride (Compound F)

1-[2-(4-pyridyl)ethyl]-4-(3-trifluoromethylphenyl)-1,2,3,6-tetrahydropyridine monohydrate dihydrochloride (Compound G)

1-[2-(4-methylphenyl)ethyl]-4-(3-trifluoromethylphenyl)-1,2,3,6-tetrahydropyridine hydrochloride (Compound H).

The above compounds, the corresponding free bases and the other pharmaceutically acceptable salts of said free bases, represent a preferred group of compounds to be used in the method of the present invention.

TABLE

| | FECAL EXCRETION IN RATS | |
|---|---|---|
| | AI-1g (mg/kg) | |
| Compound | s.c. | p.o. |
| A | n.d. | 16 |
| B | n.d. | 1.3 |
| C | 6 | 3.9 |
| D | 4 | 13 |
| E | 2 | 1.7 |
| F | 1 | 0.6 |
| G | 1 | 5 |
| H | 3 | 2.3 | n.d. = not determined

As illustrated in the above Table, the compounds of formula (I) are active as anticonstipant agents at very low doses; particularly active are Compounds F, B, E, H, and C which represent, together with the corresponding free bases and the other pharmaceutically acceptable salts thereof, a particularly preferred group of active principles to be used in the method of the present invention.

The compounds of formula (I) as well as their pharmaceutically acceptable salts can be administered orally, sublingually, transdermically or parenterally. The amount of active principle which has to be administered for the treatment of intestinal motility disorders will depend, as usual, on many factors, including the type of treatment, whether prophylactic or curative, the nature and severity of the disorders to be treated, the weight of the patients and the administration route.

In humans, a suitable dose may vary from 0.2 to 150 mg, one to three times a day, the lower doses being appropriate for children.

For the preparation of the pharmaceutical compositions according to the present invention, the active principles (the compounds of formula (I) as well as their pharmaceutically acceptable salts) are advantageously formulated in dosage unit forms comprising from 0.2 to 150 mg, preferably from 0.5 to 50 mg, of active principle, either alone or in admixture with a pharmaceutical carrier. As an example, when a solid composition is prepared in the form of tablets, the main active ingredient is mixed with a pharmaceutical carrier such as gelatin, starch, lactose, magnesium stearate, talc, arabic gum, and the like. The tablets may be coated with saccharose or other appropriate materials or they may be treated so that their activity is extended or delayed and they continuously release a predetermined amount of active principle.

A preparation in capsules may easily be obtained by mixing the active ingredient with a diluent and by filling the obtained mixture into soft or hard capsules.

A preparation in the form of a syrup or an elixir may contain the active ingredient jointly with a sweetening agent, possibly acaloric, methylparaben and propylparaben as antiseptics, as well as with a flavoring agent and a suitable dye, in a liquid vehicle.

Water-dispersible powders or granulates will contain the active ingredient, in admixture with dispersing or wetting agents, or with suspending agents such as polyvinylpyrrolidone and the like agents, and optionally with sweetening and/or flavouring agents.

The active principle may also be formulated in the form of microcapsules, optionally with one or more carriers or additives. For sublingual administration, microtablets or microcapsules can be prepared which placed under the tongue will rapidly dissolve. Said microtablets and microcapsules will generally contain the active ingredient in admixture with wetting and/or dispersing agents and optionally with one or more absorption enhancers.

For transdermic administration, the use of polymeric matrices for the continuous and preferably sustained release of the active principle can be envisaged as well as the use of the active principle as a microemulsion, with excipients suitable for contact with the skin.

For parenteral administration, aqueous suspensions, isotonic saline solutions, or sterile injectable solutions are used, which contain pharmacolologically compatible dispersing and/or wetting agents, e.g. propylene glycol or butylene glycol.

The pharmaceutical compositions of the present invention may be prepared according to the conventional methods known in industrial pharmacy (see Remington's Pharmaceutical Sciences—Mack Publishing Co.). Examples of suitable pharmaceutical compositions and of the methods for their preparation have already been described in EP-60176 and EP-101,381.

The following Examples further illustrate the invention without however limiting it.

PREPARATION

Compound H

A mixture of 2-chloro-1-(p-tolyl)ethane (9.5 g), 4-(3-trifluoromethylphenyl)-1,2,3,6-tetrahydropyridine free base (13.9 g), triethylamine (7 g) and absolute ethanol (150 ml) is heated to the reflux temperature for 20 hours. The solvent is then evaporated off under reduced pressure and the residue is taken up with ethyl ether (150 ml) and washed three times with water (30 ml). The organic phase is dried over sodium sulphate, and evaporated to dryness under reduced pressure.

1-[2-(p-Tolyl)ethyl]-4-(3-trifluoromethylphenyl)-1,2,3,6-tetrahydropyridine, free base, is thus obtained as an oily product. By treating the free base with hydrogen chloride saturated isopropanol (30 ml), the corresponding hydrochloride is obtained which is recovered by filtration and crystallized from isopropanol (60 ml).

Yield: 4.7 g. M.p. 263°-66° C.

EXAMPLE 1

1,000 Tablets containing Compound F as the active principle are prepared starting from the following ingredients:

| | |
|---|---|
| Compound F | 2.5 g |
| Lactose | 50.0 g |
| Microcrystalline cellulose | 15.0 g |
| Dried corn starch | 20.0 g |
| Magnesium stearate | 2.5 g | crushing the active ingredient to a particle dimension of 0.4 mm by passing it through a 0.4 mm sieve, mixing the crushed mixture with the other constituents and compressing to form the tablets.

Each tablet thus contains 2.0 mg, calculated as the free base, of active principle.

EXAMPLES 2 to 4

By following the same procedure described above but replacing 2.5 g of Compound F with 3.2 g, 5.1 g, and 6.4 g, 1000 tablets are obtained, each containing respectively 2.5 mg, 4 mg, and 5 mg, calculated as the free base, of active principle.

EXAMPLE 5

1,000 Tablets containing Compound F as the active ingredient are prepared from the following constituents:

| | |
|---|---|
| Compound F | 25.5 g |
| Lactose | 79.0 g |
| Corn starch | 90.0 g |
| Talc | 5.0 g |
| Magnesium stearate | 0.5 g |

Each tablet thus contains 20 mg, calculated as the free base, of active principle.

EXAMPLE 6

By following the procedure of Example 1, but replacing 2.5 g of Compound F with 2.2 g of Compound B, 1,000 tablets are obtained, each containing 2.0 mg, calculated as the free base, of active principle.

EXAMPLES 7 to 9

By operating as above, but starting from 2.7 g, 4.4 g, and 5.4 g instead of 2.2 g of Compound B, 1,000 tablets are obtained, each containing respectively 2.5 mg, 4 mg, and 5 mg, calculated as the free base, of active principle.

EXAMPLE 10

1,000 Capsules, each containing 20 mg, calculated as the free base, of active principle, are prepared from the following constituents:

| | |
|---|---|
| Compound B | 21.9 g |
| Microcrystalline cellulose | 77.0 g |
| Amorphous silica gel | 1.0 g | thoroughly mixing together the above ingredients and filling the obtained mixture into size 4 hard gelatin capsules.

We claim:

1. A compound which is 1-[2-(p-tolyl)ethyl]-4-(3-trifluoromethylphenyl)-1,2,3,6-tetrahydropyridine and its pharmaceutically acceptable salts.

2. A pharmaceutical composition which comprises an effective amount of a compound according to claim 1.

3. A pharmaceutical composition for the prophylaxis and/or treatment of intestinal motility disorders in mammals which comprises a prophylactically and/or therapeutically effective amount of a compound of claim 1 and a pharmaceutically acceptable carrier.

4. The composition of claim 3 in dosage unit form containing from 0.2 to 150 mg of the tetrahydropyridine compound and its pharmaceutically acceptable salts.

5. The composition of claim 3 wherein the intestinal motility disorder is constipation.

* * * * *